United States Patent
Addison et al.

(10) Patent No.: US 10,165,953 B2
(45) Date of Patent: Jan. 1, 2019

(54) METHODS AND SYSTEMS FOR RECALIBRATING A BLOOD PRESSURE MONITOR WITH MEMORY

(71) Applicant: Nellcor Puritan Bennett Ireland, Mervue, Galway (IE)

(72) Inventors: Paul Stanley Addison, Edinburgh (GB); James N. Watson, Dunfermline (GB)

(73) Assignee: Nellcor Puritan Bennett Ireland, Galway (IE)

(*) Notice: Subject to any disclaimer, the term of this patent is extended or adjusted under 35 U.S.C. 154(b) by 49 days.

(21) Appl. No.: 15/076,552

(22) Filed: Mar. 21, 2016

(65) Prior Publication Data

US 2016/0198963 A1    Jul. 14, 2016

Related U.S. Application Data

(63) Continuation of application No. 14/469,135, filed on Aug. 26, 2014, now Pat. No. 9,289,136, which is a
(Continued)

(51) Int. Cl.
*G01L 27/00* (2006.01)
*A61B 5/021* (2006.01)
(Continued)

(52) U.S. Cl.
CPC ...... *A61B 5/02141* (2013.01); *A61B 5/02125* (2013.01); *A61B 5/02416* (2013.01);
(Continued)

(58) Field of Classification Search
None
See application file for complete search history.

(56) References Cited

U.S. PATENT DOCUMENTS 3,835,840 A    9/1974  Mount
4,561,447 A   12/1985  Kawamura et al.
(Continued)

FOREIGN PATENT DOCUMENTS

EP    0443267    8/1991
EP    0755221    1/1997
(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.
(Continued)

*Primary Examiner* — Aditya Bhat
(74) *Attorney, Agent, or Firm* — Shumaker & Sieffert, P.A.

(57) ABSTRACT

Systems and methods are provided for storing and recalling metrics associated with physiological signals. It may be determined that the value of a monitored physiological metric corresponds to a stored value. In such cases, a patient monitor may determine that a calibration is not desired. In some cases, a patient monitor may recall calibration parameters associated with the stored value if it determined that the stored value corresponds to the monitored metric value.

20 Claims, 7 Drawing Sheets

Related U.S. Application Data continuation of application No. 12/956,963, filed on Nov. 30, 2010, now Pat. No. 8,825,428.

(51) Int. Cl.
*A61B 5/024* (2006.01)
*A61B 5/1455* (2006.01)
*A61B 5/00* (2006.01)
*G16H 40/40* (2018.01)

(52) U.S. Cl.
CPC ........ *A61B 5/14551* (2013.01); *A61B 5/7221* (2013.01); *A61B 5/7235* (2013.01); *G16H 40/40* (2018.01); *A61B 5/7239* (2013.01); *A61B 2560/0223* (2013.01); *A61B 2560/0271* (2013.01)

(56) References Cited

U.S. PATENT DOCUMENTS

| | | |
|---|---|---|
| 4,669,485 A | 6/1987 | Russell |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,065,765 A | 11/1991 | Eckerle |
| 5,103,831 A | 4/1992 | Niwa |
| 5,105,815 A | 4/1992 | Hall et al. |
| 5,111,817 A | 5/1992 | Clark et al. |
| 5,119,824 A | 6/1992 | Niwa |
| 5,131,400 A | 7/1992 | Harada |
| 5,163,328 A | 11/1992 | Holland |
| 5,165,416 A | 11/1992 | Shinoda et al. |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,617,868 A | 4/1997 | Harada |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias |
| 5,830,131 A | 11/1998 | Caro et al. |
| 5,832,924 A | 11/1998 | Archibald et al. |
| 5,833,618 A | 11/1998 | Caro |
| 5,842,975 A | 12/1998 | Illyes et al. |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,921,936 A | 7/1999 | Inukai et al. |
| 5,941,828 A | 8/1999 | Archibald et al. |
| 5,964,711 A | 10/1999 | Voss |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,045,509 A | 4/2000 | Caro et al. |
| 6,050,951 A | 4/2000 | Friedman et al. |
| 6,067,462 A | 5/2000 | Diab |
| 6,083,171 A | 7/2000 | Ono et al. |
| 6,095,987 A | 8/2000 | Shmulewitz |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,331,162 B1 | 12/2001 | Mitchell |
| 6,332,867 B1 | 12/2001 | Chen et al. |
| 6,350,242 B1 | 2/2002 | Doten et al. |
| 6,371,921 B1 | 4/2002 | Caro |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,984 B1 | 5/2003 | Turcott |
| 6,561,986 B2 | 5/2003 | Baura |
| 6,566,251 B2 | 5/2003 | Allen et al. |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,616,613 B1 | 9/2003 | Goodman |
| 6,626,839 B2 | 9/2003 | Doten et al. |
| 6,631,281 B1 | 10/2003 | Kastle |
| 6,645,156 B2 | 11/2003 | Oka |
| 6,648,828 B2 | 11/2003 | Friedman et al. |

(56) References Cited

U.S. PATENT DOCUMENTS

| | | | |
|---|---|---|---|
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,893,401 B2 | 5/2005 | Chen et al. |
| 6,929,610 B2 | 8/2005 | Forstner |
| 6,996,427 B2 | 2/2006 | Ali et al. |
| 7,004,907 B2 | 2/2006 | Banet |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,428,432 B2 | 9/2008 | Al-Ali et al. |
| 7,455,643 B1 | 11/2008 | Li et al. |
| 7,481,772 B2 | 1/2009 | Banet |
| 7,485,095 B2 | 2/2009 | Shusterman |
| 7,769,436 B1 | 8/2010 | Boileau et al. |
| 8,251,912 B2 | 8/2012 | Shelley et al. |
| 8,398,556 B2 | 3/2013 | Sethi et al. |
| 8,825,428 B2 | 9/2014 | Addison et al. |
| 9,289,136 B2 | 3/2016 | Addison et al. |
| 9,357,934 B2 | 6/2016 | Watson et al. |
| 9,687,161 B2 * | 6/2017 | Sethi ............... A61B 5/02007 |
| 2002/0095090 A1 | 7/2002 | Caro et al. |
| 2003/0036685 A1 * | 2/2003 | Goodman ........... A61B 5/0002 600/300 |
| 2004/0210625 A1 | 10/2004 | Bodin et al. |
| 2005/0038332 A1 | 2/2005 | Saidara et al. |
| 2005/0148885 A1 | 7/2005 | Tweed et al. |
| 2005/0192500 A1 | 9/2005 | Caro et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0122517 A1 | 6/2006 | Banet et al. |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0258926 A1 | 11/2006 | Al-Ali et al. |
| 2006/0285736 A1 | 12/2006 | Brown |
| 2006/0287603 A1 | 12/2006 | Bartnik et al. |
| 2007/0027375 A1 | 2/2007 | Melker et al. |
| 2007/0055163 A1 | 3/2007 | Asada et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0142730 A1 | 6/2007 | Laermer et al. |
| 2007/0225582 A1 | 9/2007 | Diab et al. |
| 2007/0249467 A1 | 10/2007 | Hong et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0097175 A1 | 4/2008 | Boyce et al. |
| 2008/0132798 A1 | 6/2008 | Hong et al. |
| 2008/0194932 A1 | 8/2008 | Ayers et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2009/0048241 A1 | 2/2009 | Keren |
| 2009/0247848 A1 | 10/2009 | Baker, Jr. |
| 2009/0326386 A1 | 12/2009 | Sethi et al. |
| 2009/0326393 A1 | 12/2009 | Sethi et al. |
| 2009/0326395 A1 | 12/2009 | Watson |
| 2010/0016746 A1 | 1/2010 | Hampton et al. |
| 2010/0081945 A1 | 4/2010 | Sethi et al. |
| 2010/0222653 A1 | 9/2010 | Siejko et al. |
| 2016/0198963 A1 | 7/2016 | Addison et al. |
| 2016/0262640 A1 | 9/2016 | Watson et al. |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 03-225268 | 12/2003 |
| WO | WO9111137 | 8/1991 |

OTHER PUBLICATIONS

Berne, Robert M., Levy, Matihew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. S11-S14.

Fitcheti, D., Bouthier, JD, Simon, A. CH., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, MI. Kisco, NY, Futura Publishing Co., 1994, pp. 1-446.

Fung, YC, Biomechanics: Circulation, 2nd Edition, New York, Springer, 1997, pp. 1-571.

Geddes, LA, Handbook of Blood Pressure Measurement, Clifton, New Jersey, Humana Press, 1991, pp. 1-168.

Millasseau, Sandrine C, Guigui, Franck G, Kelly, Ronan P., Prasad, Krishna, Cockcroft, John R., Ritter, James M., Chowienczyk, Philip J., "Noninvasive Assessment of the Digital Volume Pulse: Comparison with the Peripheral Pressure Pulse, Hypertension," vol. 36, No. 6, Dec. 2000, pp. 952-956.

Moyle, John TB, Hahn, Cew, Adams, Anthony P, Pulse Oximetry, Revised Edition, London, BMJ, 1998, pp. 1-140.

Nara, Andrew R., Burns, Michael P., Downs, W. Gregory, Blood Pressure, Redmond, Washington, SpaceLabs, 1989, pp. 1-109.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990, pp. 1-456.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, Feb. 1991'pp. 39-54.

(56) References Cited

OTHER PUBLICATIONS

Young, Christopher C., Mark, Jonathan B., White, William, Debree, Ashley, Vender, Jefferys., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.
Prosecution History from U.S. Appl. No. 12/956,963, dated Mar. 29, 2013 through Apr. 25, 2014, 59 pp.
Prosecution History from U.S. Appl. No. 14/469,135, dated May 7, 2015 through Feb. 19, 2016, 39 pp.

* cited by examiner

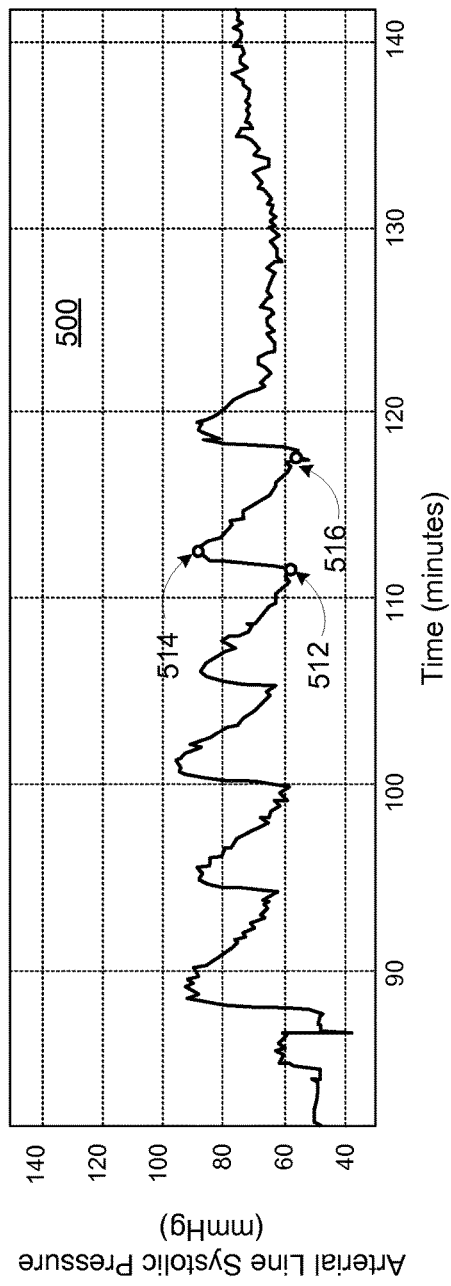
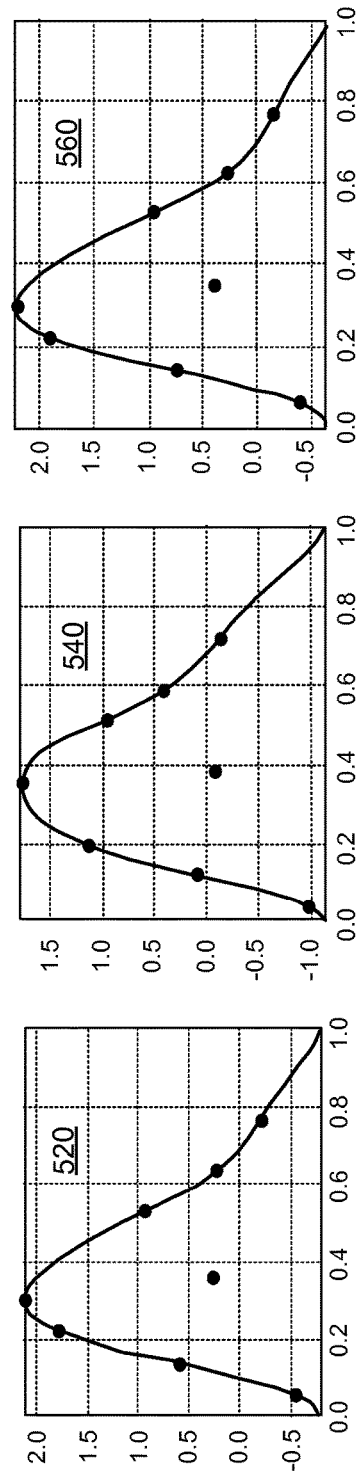
FIG. 5(a)
FIG. 5(b)
FIG. 5(c)
FIG. 5(d)

METHODS AND SYSTEMS FOR RECALIBRATING A BLOOD PRESSURE MONITOR WITH MEMORY

CROSS REFERENCE TO RELATED APPLICATIONS

This application is a continuation of U.S. patent application Ser. No. 14/469,135, filed Aug. 26, 2014, which is a continuation of U.S. patent Ser. No. 12/956,963, filed Nov. 30, 2010, now U.S. Pat. No. 8,825,428, which are incorporated by reference herein in their entireties.

SUMMARY

Continuous non-invasive blood pressure (CNIBP) monitoring systems allow a patient's blood pressure to be tracked continuously, unlike standard occlusion cuff techniques, and without the hazards of invasive arterial lines. In some embodiments, multiple pulse oximetry type sensors may be placed at multiple body sites on a patient to measure photoplethysmograph (PPG) signals. The resulting multiple PPG signals may be compared against each other to estimate the patient's blood pressure. When the locations of two sensors are at different distances from the heart or along different paths from the heart (e.g., at the finger and forehead), a differential pulse transit time (DPTT) may be determined. A DPTT may represent the difference in the arrival times of a portion of a cardiac wave between the two locations, and may be determined by comparing corresponding fiducial points in the two PPG signals (e.g., a maximum, minimum, or a notch). In some techniques, two DPTTs are determined in order to calculate multiple physiological parameters, such as systolic and diastolic blood pressure. These DPTTs may be determined during different phases of the PPG signal representing different physiological occurrences. For example, one DPTT may be determined when the cardiovascular system is in a systolic state and a second DPTT may be determined when the cardiovascular system is in a diastolic state.

During physiological monitoring of a patient with a patient monitoring system, recalibration of the patient monitoring system may be desired. For example, a CNIBP system may be periodically calibrated with a NIBP system. It may be desirous in some instances to reduce the number of calibrations that are performed. For example, an inflatable cuff type NIBP system may be used to calibrate a PPG-based CNIBP system, and a reduction in the number of cuff inflations may be desirous. In some circumstances, performing a calibration is likely to result in calibration parameters similar to those of a previous calibration.

Systems and methods are provided herein for calibrating a patient monitoring system with stored calibration parameters. Calibration parameters may be stored in a suitable memory device, and recalled during suitable calibration conditions. Values of one or more metrics associated with one or more physiological signals (e.g., PPG signals) may be monitored by a patient monitoring system and compared with stored metric values. If it is determined by the patient monitoring system that the value of the monitored metric corresponds to a stored metric value, the patient monitoring system may recall calibration parameters associated with the stored value.

In some embodiments, for example, metrics may be stored in any suitable database. Calibration parameters associated with the stored metrics may also be stored in any suitable database (e.g., the same database where the metrics are stored). Metrics may include signal morphology parameters such as, for example, pulse wave area, pulse wave skew, derivatives of a signal, heart rate, length of a pulse upstroke, any other suitable metric or any combination thereof. Metrics derived from a physiological signal may change due to, for example, effects of vasoactive drugs, patient movement, or other factors which may change arterial compliance.

In some embodiments, a patient monitoring system may monitor one or more metrics derived from a physiological signal. One or more metrics of the physiological signal may change over time due to any suitable cause or combination of causes. In some circumstances, following the temporal change in the one or more metrics, the values of the one or more metrics may return to or about their past values as computed prior to the change. The patient monitoring system may then recall stored calibration parameters associated with the past values rather than performing an actual recalibration. For example, a CNIBP device calibrated with initial calibration parameters may be used to monitor a physiological metric associated with a patient. At a particular time, a vasoactive drug may be administered, and the value of the metric may change. At a particular time after the drug was administered, the value of the metric may return to the metric's value prior to the drug administration. The patient monitoring system may, in response to the return of the metric's value, revert to the stored initial calibration parameters rather than initiating a new NIBP (e.g., cuff device) calibration to determine new calibration parameters.

The methods and systems of the present disclosure will be illustrated with reference to the monitoring of a physiological signal (which may be a PPG signal). However, it will be understood that the disclosure is not limited to monitoring physiological signals and is usefully applied within a number of signal monitoring settings.

BRIEF DESCRIPTION OF THE DRAWINGS

The above and other features of the present disclosure, its nature and various advantages will be more apparent upon consideration of the following detailed description, taken in conjunction with the accompanying drawings in which:

FIG. 5(a) shows an illustrative time series of a blood pressure measurement in accordance with an embodiment;

FIG. 5(b) shows an illustrative portion of a PPG signal corresponding to some data of FIG. 5(a) in accordance with an embodiment;

FIG. 5(c) shows an illustrative portion of a PPG signal corresponding to some data of FIG. 5(a) in accordance with an embodiment;

FIG. 5(d) shows an illustrative portion of a PPG signal corresponding to some data of FIG. 5(a) in accordance with an embodiment;

DETAILED DESCRIPTION

Figure 1:
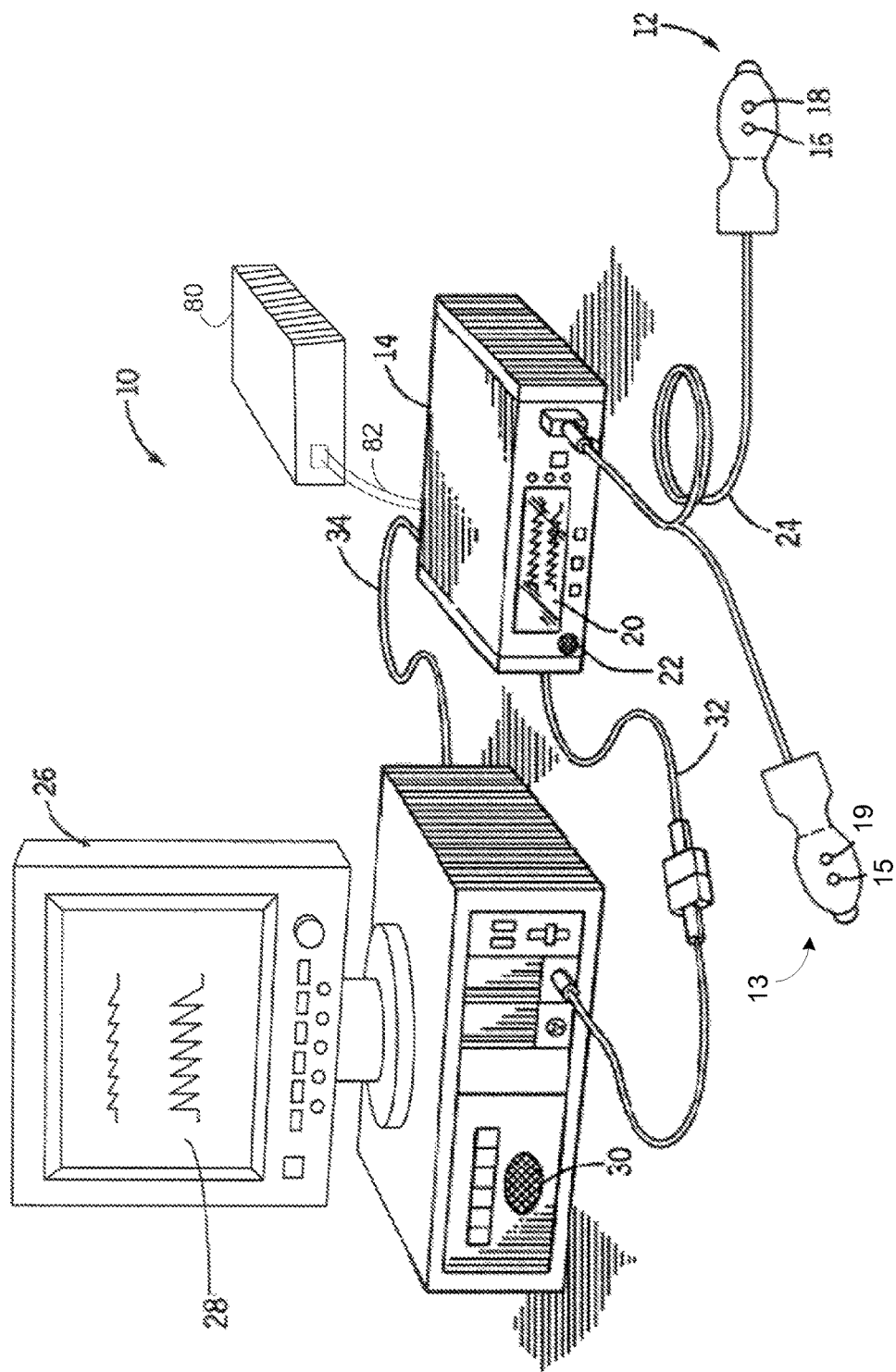
FIG. 1 shows an illustrative patient monitoring system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate and blood pressure.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_O(\lambda)\exp(-(s\beta_O(\lambda)+(1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_O, \beta_r$=empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_O - (s\beta_O + (1-s)\beta_r)l. \quad (2)$$

2. Eq. 2 is then differentiated with respect to time to yield $$\frac{d\log I}{dt} = -(s\beta_O + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_O(\lambda_R) + (1-s)\beta_r(\lambda_R)}{s\beta_O(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_O(\lambda_{IR}) - \beta_r(\lambda_{IR})) - \frac{d\log I(\lambda_{IR})}{dt}(\beta_O(\lambda_R) - \beta_r(\lambda_R))}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R, \tag{8}$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_O(\lambda_{IR}) - \beta_r(\lambda_{IR})) - \beta_O(\lambda_R) + \beta_r(\lambda_R)}. \tag{9}$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \tag{10}$$

Eq. 8 becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \tag{11}$$

$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$

$$= R,$$

which defines a cluster of points whose slope of y versus x will give R when $$x = [I(t_2,\lambda_{IR}) - I(t_1,\lambda_{IR})]I(t_1,\lambda_R), \tag{12}$$

and $$y = [I(t_2,\lambda_R) - I(t_1,\lambda_R)]I(t_1,\lambda_{IR}) \tag{13}$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In an embodiment, sensor unit 12 may be part of a continuous, non-invasive blood pressure (CNIBP) monitoring system and/or an oximeter. Sensor unit 12 may include an emitter 16 for emitting light at one or more wavelengths into a patient's tissue. A detector 18 may also be provided in sensor 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units, such as sensor unit 13, which may take the form of any of the embodiments described herein with reference to sensor unit 12. For example, sensor unit 13 may include emitter 15 and detector 19. Sensor unit 13 may be the same type of sensor unit as sensor unit 12, or sensor unit 13 may be of a different sensor unit type than sensor unit 12. Sensor units 12 and 13 may be capable of being positioned at two different locations on a subject's body; for example, sensor unit 12 may be positioned on a patient's forehead, while sensor unit 13 may be positioned at a patient's fingertip.

Sensor units 12 and 13 may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include a plurality of sensors forming a sensor array in lieu of either or both of sensor units 12 and 13. Each of the sensors of a sensor array may be a complementary metal oxide semiconductor (CMOS) sensor. Alternatively, each sensor of an array may be charged coupled device (CCD) sensor. In an embodiment, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more of sensor units 12 and 13 in accordance with the systems and techniques disclosed herein. It is understood that any number of sensors measuring any number of physiological signals may be used to determine physiological information in accordance with the techniques described herein.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as in a sensor designed to obtain pulse oximetry data from a patient's forehead.

In an embodiment, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., heart rate, blood pressure, blood oxygen saturation) based at least in part on data relating to light emission and detection received from one or more sensor units such as sensor units 12 and 13. In an alternative embodiment, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In an embodiment, the monitor 14 includes a blood pressure monitor. In alternative embodiments, the system 10 includes a stand-alone blood pressure monitor in communication with the monitor 14 via a cable or a wireless network link.

In an embodiment, sensor unit 12 may be communicatively coupled to monitor 14 via a cable 24. However, in other embodiments, a wireless transmission device (not shown) or the like may be used instead of or in addition to cable 24.

In the illustrated embodiment, system 10 includes a multi-parameter patient monitor 26. The monitor 26 may include a cathode ray tube display, a flat panel display (as shown) such as a liquid crystal display (LCD) or a plasma display, or may include any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood oxygen saturation generated by monitor 14 (referred to as an "SpO$_2$" measurement), pulse rate information from monitor 14 and blood pressure from monitor 14 on display 28. Multi-parameter patient monitor 26 may include a speaker 30.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable signal calibration device. Calibration device 80 may be communicatively coupled to monitor 14 via cable 82, and/or may communicate wirelessly (not shown). In other embodiments, calibration device 80 is completely integrated within monitor 14. For example, calibration device 80 may take the form of any invasive or non-invasive blood pressure monitoring or measuring system used to generate reference blood pressure measurements for use in calibrating a CNIBP monitoring technique as described herein. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference signal measurements obtained from some other source (e.g., an external invasive or non-invasive physiological measurement system).

Calibration device 80 may also access reference signal measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle or a different periodic cycle. Reference blood pressure measurements may be generated when recalibration is triggered.

Figure 2:
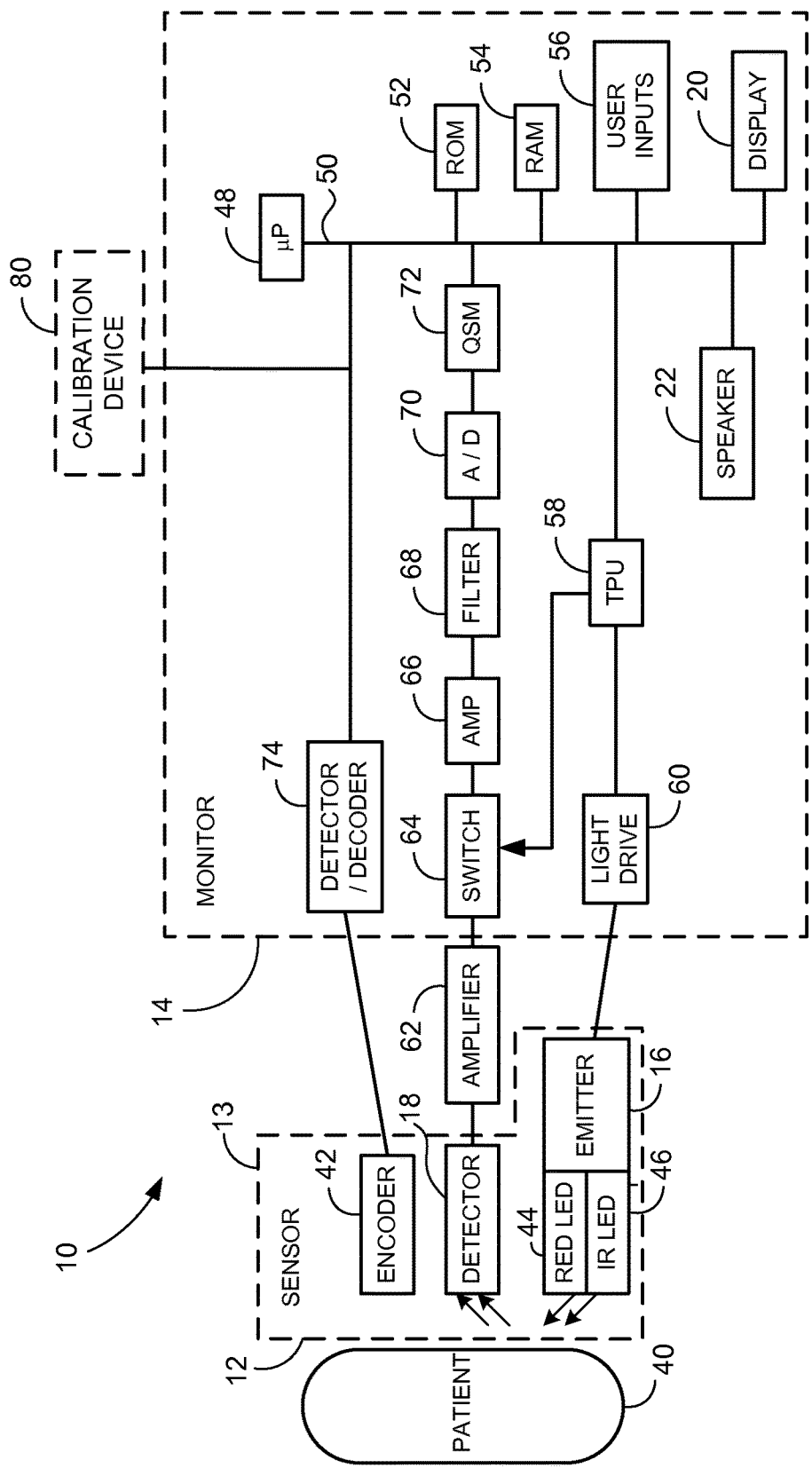
FIG. 2 shows a block diagram of the illustrative patient monitoring system of FIG. 1 coupled to a patient in accordance with an embodiment.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2. Because sensor units 12 and 13 may include similar components and functionality, only sensor unit 12 will be discussed in detail for ease of illustration. It will be understood that any of the concepts, components, and operation discussed in connection with sensor unit 12 may be applied to sensor unit 13 as well (e.g., emitter 16 and detector 18 of sensor unit 12 may be similar to emitter 15 and detector 19 of sensor unit 13). It will be noted that patient monitoring system 10 may include one or more additional sensor units or probes, which may take the form of any of the embodiments described herein with reference to sensor units 12 and 13 (FIG. 1). These additional sensor units included in system 10 may take the same form as sensor unit 12, or may take a different form. In an embodiment, multiple sensors (distributed in one or more sensor units) may be located at multiple different body sites on a patient.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In one embodiment, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor emits only a Red light while a second emits only an IR light. In another example, the wavelengths of light used are selected based on the specific location of the sensor.

It will be understood that, as used herein, the term "light" may refer to energy produced by radiation sources and may include one or more of ultrasound, radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which, for example, blood pressure and other measurements may be determined based at least in part on the signal or signals received at sensor unit 12. For example, some pulse oximetry sensors rely on equations to relate an area under a portion of a photoplethysmograph (PPG) signal corresponding to a physiological pulse to determine blood pressure. These equations may contain coefficients that depend upon a patient's physiological characteristics as stored in encoder 42. Encoder 42 may, for instance, be a coded resistor which stores values corresponding to the type of sensor unit 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, remote memory 90, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

Remote memory 90 may include any suitable volatile memory, non-volatile memory, or any combination thereof. Remote memory 90 may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. In some embodiments, remote memory 90 may be separate and remote from other components included in the patient monitoring system. For example, in some embodiments, remote memory 90 may be included in a database server, application server, remote processing facility or device, cloud-based information storage system, any other suitable accessible information storage system or device, or any suitable combination thereof.

Communications path 92 may, in some embodiments, couple remote memory 90 to bus 50 via a suitable interface, or any other suitable component of patient monitoring system 10. Communication path 92 may include any suitable type of wired network (e.g., local area network, ethernet, universal serial bus), wireless network (e.g., WiFi, Global System for Mobile Communication, BLUETOOTH), optical communications path (e.g., a fiber optic network), any other suitable communications path, or any suitable combination thereof.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 fills up. In one embodiment, there may be multiple separate parallel paths having components equivalent to amplifier 66, filter 68, and/or A/D converter 70 for multiple light wavelengths or spectra received.

In an embodiment, microprocessor 48 may determine the patient's physiological parameters, such as $SpO_2$, pulse rate, and/or blood pressure, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals or otherwise identify noise components in order to prevent them from affecting measurements of physiological parameters derived from the sensor signals.

Pulse oximeters, in addition to providing other information, can be utilized for continuous non-invasive blood pressure monitoring. As described in Chen et al., U.S. Pat. No. 6,599,251, the entirety of which is incorporated herein by reference, PPG and other pulse signals obtained from multiple probes can be processed to calculate the blood pressure of a patient. In particular, blood pressure measurements may be derived based on a comparison of time differences between certain components of the pulse signals detected at each of the respective probes. As described in U.S. patent application Ser. No. 12/242,238, filed on Sep. 30, 2008 and entitled "Systems and Methods For Non-Invasive Blood Pressure Monitoring," the entirety of which is incorporated herein by reference, blood pressure can also be derived by processing time delays detected within a single PPG or pulse signal obtained from a single pulse oximeter probe. In addition, as described in U.S. patent application Ser. No. 12/242,867, filed on Sep. 30, 2008 and entitled "Systems and Methods For Non-Invasive Continuous Blood Pressure Determination," the entirety of which is incorporated herein by reference, blood pressure may also be obtained by calculating the area under certain portions of a pulse signal. Finally, as described in U.S. patent application Ser. No. 12/242,862, filed on Sep. 30, 2008 and entitled "Systems and Methods For Maintaining Blood Pressure Monitor Calibration," the entirety of which is incorporated herein by reference, a blood pressure monitoring device may be recalibrated in response to arterial compliance changes.

As described above, some CNIBP monitoring techniques utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p = a + b \cdot \ln(T) \quad (14)$$

where a and b are constants that may be dependent upon the nature of the subject and the nature of the signal detecting devices. Other suitable equations using an elapsed time between corresponding points of a pulse signal may also be used to derive an estimated blood pressure measurement.

In an embodiment, Eq. 14 may include a non-linear function which is monotonically decreasing and concave upward in T in a manner specified by the constant parameters (in addition to or instead of the expression of Eq. 14). Eq. 14 may be used to calculate an estimated blood pressure from the time difference T between corresponding points of a pulse signal received by two sensors or probes attached to two different locations of a subject.

In an embodiment, constants a and b in Eq. 14 above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

In an embodiment, the calibration may include performing calculations mathematically equivalent to $$a = c_1 + \frac{c_2(P_0 - c_1)}{\ln(T_0) + c_2} \text{ and} \quad (15)$$

$$b = \frac{P_0 - c_1}{\ln(T_0) + c_2} \quad (16)$$

to obtain values for the constants a and b, where $c_1$ and $c_2$ are parameters that may be determined, for example, based on empirical data.

In an embodiment, the calibration may include performing calculations mathematically equivalent to $$a = P_0 - (c_3 T_0 + c_4) \ln(T_0) \quad (17)$$

and $$b = c_3 T_0 + c_4 \quad (18)$$

where a and b are first and second parameters and $c_3$ and $c_4$ are parameters that may be determined, for example, based on empirical data.

Parameters $c_1$, $c_2$, $c_3$, and $c_4$ may be predetermined constants empirically derived using experimental data from a number of different patients. A single reference blood pressure reading from a patient, including reference blood pressure $P_0$ and elapsed time $T_0$ from one or more signals corresponding to that reference blood pressure, may be combined with such inter-patient data to calculate the blood pressure of a patient. The values of $P_0$ and $T_0$ may be referred to herein as a calibration point. According to this example, a single calibration point may be used with the predetermined constant parameters to determine values of constants a and b for the patient (e.g., using Eqs. 15 and 16 or 17 and 18). The patient's blood pressure may then be calculated using Eq. 14. Recalibration may be performed by collecting a new calibration point and recalculating the constants a and b used in Eq. 14. Calibration and recalibration may be performed using calibration device 80 (FIG. 1).

In an embodiment, multiple calibration points from a patient may be used to determine the relationship between the patient's blood pressure and one or more PPG signals. This relationship may be linear or non-linear and may be extrapolated and/or interpolated to define the relationship over the range of the collected recalibration data. For example, the multiple calibration points may be used to determine values for parameters $c_1$ and $c_2$ or $c_3$ and $c_4$ (described above). These determined values will be based on information about the patient (intra-patient data) instead of information that came from multiple patients (inter-patient data). As another example, the multiple calibration points may be used to determine values for parameters a and b (described above). Instead of calculating values of parameters a and b using a single calibration point and predetermined constants, values for parameters a and b may be empirically derived from the values of the multiple calibration points. As yet another example, the multiple calibration points may be used directly to determine the relationship between blood pressure and PPG signals. Instead of using a predefined relationship (e.g., the relationship defined by Eq. 14), a relationship may be directly determined from the calibration points.

Additional examples of continuous and non-invasive blood pressure monitoring techniques are described in Chen et al., U.S. Pat. No. 6,566,251, which is hereby incorporated by reference herein in its entirety. The technique described by Chen et al. may use two sensors (e.g., ultrasound or photoelectric pulse wave sensors) positioned at any two locations on a subject's body where pulse signals are readily detected. For example, sensors may be positioned on an earlobe and a finger, an earlobe and a toe, or a finger and a toe of a patient's body.

Figure 3:
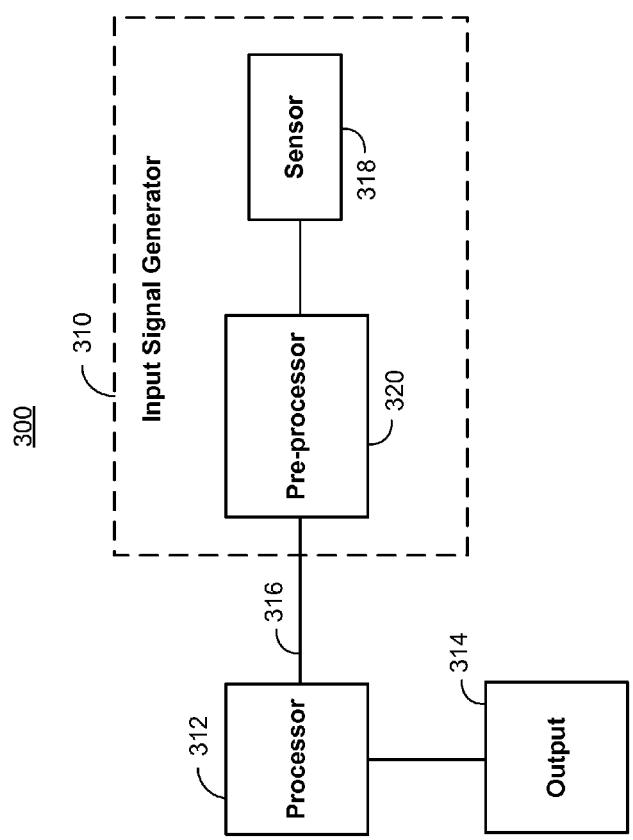
FIG. 3 shows a block diagram of an illustrative signal processing system in accordance with an embodiment.

FIG. 3 is an illustrative signal processing system 300 in accordance with an embodiment that may implement the non-invasive blood pressure techniques described herein. In this embodiment, input signal generator 310 generates an input signal 316. As illustrated, input signal generator 310 may include pre-processor 320 coupled to sensor 318, which may provide input signal 316. In an embodiment, pre-processor 320 may be an oximeter and input signal 316 may be a PPG signal. In an embodiment, pre-processor 320 may be any suitable signal processing device and input signal 316 may include one or more PPG signals and one or more other physiological signals, such as an electrocardiogram (ECG) signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a predetermined set of processing operations to the signal provided by sensor 318 to produce input signal 316 that can be appropriately interpreted by processor 312, such as performing A/D conversion. Pre-processor 320 may also perform any of the following operations on the signal provided by sensor 318: reshaping the signal for transmission, multiplexing the signal, modulating the signal onto carrier signals, compressing the signal, encoding the signal, and filtering the signal.

In an embodiment, signal 316 may include PPG signals at one or more frequencies, such as a Red PPG signal and an IR PPG signal. In an embodiment, signal 316 may include signals measured at one or more sites on a patient's body, for example, a patient's finger, toe, ear, arm, or any other body site. In an embodiment, signal 316 may include multiple types of signals (e.g., one or more of an ECG signal, an EEG signal, an acoustic signal, an optical signal, a signal representing a blood pressure, and a signal representing a heart rate). Signal 316 may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

In an embodiment, signal 316 may be coupled to processor 312. Processor 312 may be any suitable software, firmware, hardware, or combination thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, be configured of analog electronic components. Processor 312 may perform the calculations associated with the information determination techniques of the present disclosure as well as the calculations associated with any calibration of processing system 300 or other auxiliary functions. For example, processor 312 may locate one or more fiducial points in one or more signals, determine one or more DPTTs, and compute one or more of a systolic blood pressure, a diastolic blood pressure and a mean arterial pressure. Processor 312 may perform any suitable signal processing of signal 316 to filter signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the patient. Additional input signals may be used by processor 312 in any of the calculations or operations it performs in accordance with processing system 300.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to blood pressure monitoring, including current blood pressure calibration values, blood pressure monitoring calibration thresholds, and patient blood pressure history. In an embodiment, processor 312 may store physiological measurements or previously received data from signal 316 in a memory device for later retrieval. In an embodiment, processor 312 may store calculated values, such as a systolic blood pressure, a diastolic blood pressure, a blood oxygen saturation, a differential pulse transit time, a fiducial point location or characteristic, or any other calculated values, in a memory device for later retrieval.

Processor 312 may be coupled to a calibration device. This coupling may take any of the forms described above with reference to calibration device 80 within system 10. For example, the calibration device may be a stand-alone device that may be in wireless communication with processor 312, or may be completely integrated with processor 312.

Processor 312 may be coupled to a calibration device that may generate, or receive as input, reference measurements for use in calibration calculations. This coupling may occur through a recalibration signal transmitted via a wired or wireless communications path. In an embodiment, processor 312 is capable of transmitting a command to calibration device 80 to initiate a recalibration procedure.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor units 12 and 13 (FIGS. 1 and 2) and monitor 14 (FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the patient (e.g., a watch, other piece of jewelry, or a cellular telephone). In such embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In such embodiments, a wireless transceiver (not shown) may also be included in system 300 to enable wireless communication with other components of system 10. For example, pre-processor 320 may output signal 316 over BLUETOOTH, 802.11, WiFi, WiMax, cable, satellite, Infrared, or any other suitable transmission scheme. In an embodiment, a wireless transmission scheme may be used between any communicating components of system 300.

Pre-processor 320 or processor 312 may determine the locations of pulses within a periodic signal 316 (e.g., a PPG signal) using a pulse detection technique. For ease of illustration, the following pulse detection techniques will be described as performed by processor 312, but any suitable processing device (e.g., pre-processor 320) may be used to implement any of the techniques described herein.

Figure 4:
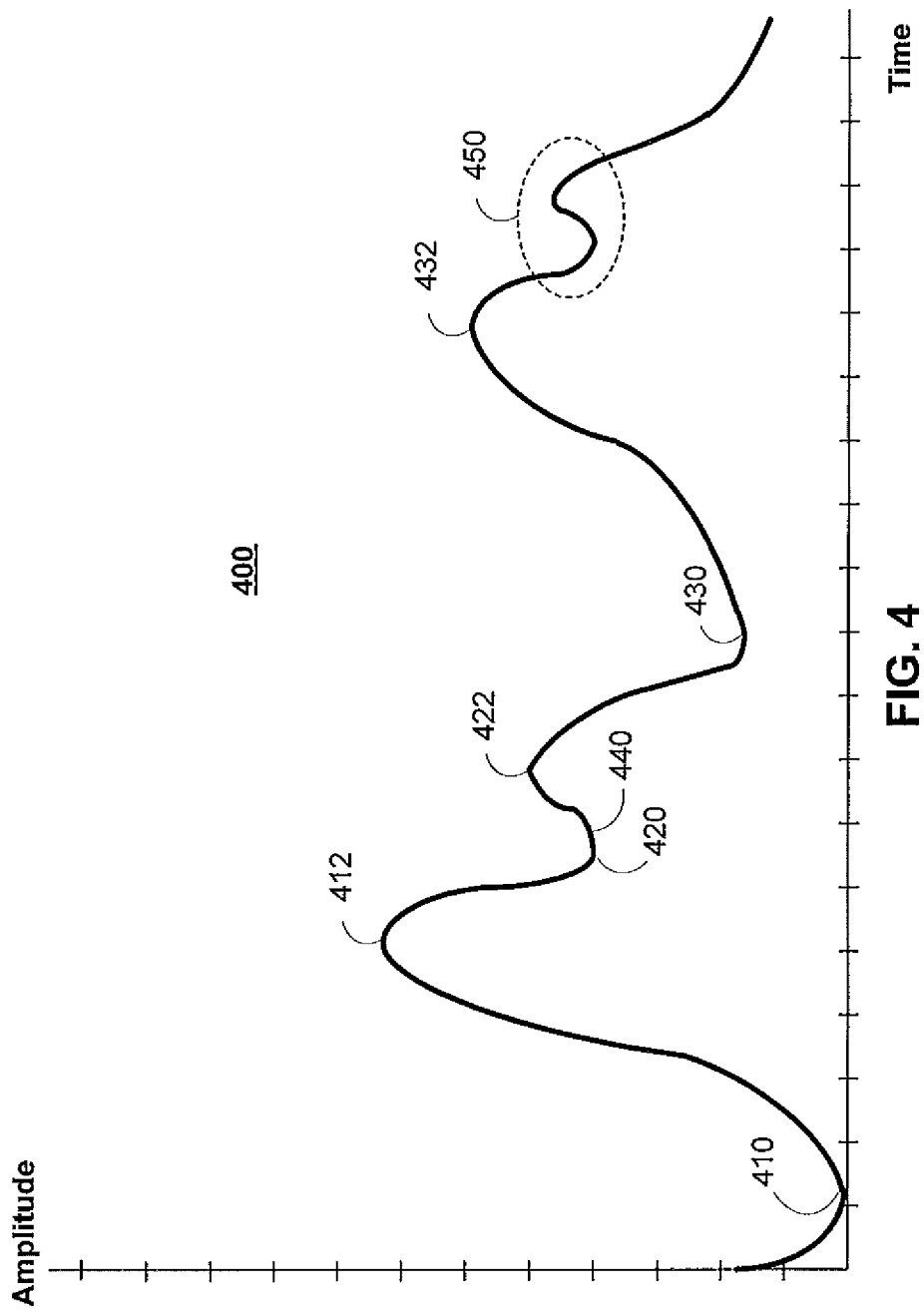
FIG. 4 shows an illustrative signal which may be analyzed in accordance with an embodiment.

An illustrative PPG signal 400 is depicted in FIG. 4. Processor 312 may receive PPG signal 400, and may identify local minimum point 410, local maximum point 412, local minimum point 420, and local maximum point 422 in the PPG signal 400. Processor 312 may pair each local minimum point with an adjacent maximum point. For example, processor 312 may pair points 410 and 412 to identify one segment, points 412 and 420 to identify a second segment, points 420 and 422 to identify a third segment and points 422 and 430 to identify a fourth segment. The slope of each segment may be measured to determine whether the segment corresponds to an upstroke portion of the pulse (e.g., a positive slope) or a downstroke portion of the pulse (e.g., a negative slope) portion of the pulse. A pulse may be defined as a combination of at least one upstroke and one downstroke. For example, the segment identified by points 410 and 412 and the segment identified by points 412 and 430 may define a pulse.

According to an embodiment, PPG signal 400 may include a dichrotic notch 450 or other notches (not shown) in different sections of the pulse (e.g., at the beginning (referred to as an ankle notch), in the middle (referred to as a dichrotic notch), or near the top (referred to as a shoulder notch)). Notches (e.g., dichrotic notches) may refer to secondary turning points of pulse waves as well as inflection points of pulse waves. Processor 312 may identify notches and either utilize or ignore them when detecting the pulse locations. In some embodiments, processor 312 may compute the second derivative of the PPG signal to find the local minima and maxima points and may use this information to determine a location of, for example, a dichrotic notch. Additionally, processor 312 may interpolate between points in signal 316 or between points in a processed signal using any interpolation technique (e.g., zero-order hold, linear interpolation, and/or higher-order interpolation techniques). Some pulse detection techniques that may be performed by processor 312 are described in more detail in co-pending, commonly assigned U.S. patent application Ser. No. 12/242,908, filed Sep. 30, 2008 and entitled "SYSTEMS AND METHODS FOR DETECTING PULSES IN A PPG SIGNAL," which is incorporated by reference herein in its entirety.

Metrics may be used to characterize or otherwise describe a physiological signal. Metrics may include suitable signal values, signal morphologies, output values from suitable operations performed on a signal or other metric, any other suitable mathematical characterizations, or any suitable combinations thereof. For example, metrics may include pulse wave area (PWA), rate of change computed at one or more points of a time series (e.g., derivative of any suitable order of a signal), statistics of a signal (e.g., mean, moment of any suitable order, regression parameters), offset of a signal from a baseline, interval of portion of a signal (e.g., length of upstroke), relative position of a fiducial point of a signal (e.g., dichrotic notch position), any other suitable metric or change thereof, or any suitable combinations thereof. For example, in some embodiments, the skewness (e.g., the standardized third central moment) of a pulse wave may be monitored.

Metrics may include mathematical manipulations of other metrics such as, for example, the value of an integral of a portion of a blood pressure measurement time series, the skewness of a derivative of a PPG signal, or any other suitable mathematical manipulations. In some embodiments, metrics may be computed from averaged, filtered, scaled, or otherwise processed physiological signals. For example, a derivative may be computed from a suitable ensemble average of pulse waves.

The term "pulse wave" as used herein refers to a portion of a PPG signal corresponding to a physiological pulse.

A patient monitoring system may determine that values of one or more metrics associated with a physiological signal correspond to stored values. The determination may be based at least in part on a comparison of metric values to stored values by, for example, computing a difference. For example, a patient monitoring system may compute a current PWA of a current PPG signal by integrating a suitable portion of the PPG signal. The patient monitoring system may search among stored values of PWA associated with previous PPG signals. The patient monitoring system may compute a difference between the current PWA value and at least one of the stored PWA values. If the patient monitoring system determines that the difference in the current and stored PWA values is below a threshold, then the patient monitoring system may determine that the PWAs correspond to each other. Thresholds may be predetermined, dynamic, constant, or any other suitable type of value, or any suitable combination thereof. For example, in some embodiments, a threshold may be ten percent of a metric value such that if the difference between a value of a monitored metric and a stored value is less than ten percent of the monitored metric, the values are determined to correspond. The selection of this threshold may be determined through consideration of previously acquired empirical data and the required accuracy. In some embodiments, the required accuracy may change with currently reported blood pressure. For example, if a current blood pressure measurement is outside normal physiological ranges, the required accuracy may be tighter and the threshold may be set to encourage a cuff inflation, or true recalibration, rather than rely on an estimate calculated using historical data. In some embodiments, a threshold may be set with respect to a historical variation of the monitored metric, for example, at a fraction (e.g., 0.5) of one standard deviation of the historic values of the monitored metric over a period of time. Any suitable threshold may be used to aid in determining whether values correspond to each other. In some embodiments, the patient monitoring system may determine whether a value of a monitored metric and a stored value to not correspond to one another.

In some embodiments, a difference vector including differences between values of monitored metrics and stored values may be computed by the patient monitoring system. The Euclidean norm, or "norm", of such a vector may provide an indication of how closely the collective values of monitored metrics correspond to stored values. For example, a patient monitoring system may compute differences between monitored values and a set of stored values of PWA, pulse wave skew, and length of pulse wave upstroke, and arrange the difference in each metric value in a difference vector. The patient monitoring system may compute the norm of the difference vector. If the norm is below a threshold value, the patient monitoring system may determine that the current metrics correspond to the stored metrics. Any suitable combination of differences or other comparisons (e.g., norms, conditional probabilities) may be used by a patient monitoring system to determine whether values correspond.

Shown in FIG. 5(a) is illustrative time series 500 of a blood pressure measurement in accordance with some embodiments. Changes in blood pressure, or other suitable physiological metrics, may occur during patient monitoring. Changes in blood pressure, arterial compliance, or other physiological metrics, may result from, for example, administration of vasoactive drugs, changes in patient position, patient activity, any other suitable event which may change the morphology of a physiological signal or metric, or any combination thereof. In some embodiments, a patient monitoring system may be recalibrated in response to changes in, for example, a PPG signal, a metric derived from a PPG signal, any other suitable signal or metric, or any suitable combination thereof.

Time series 500 shown in FIG. 5(a) includes multiple changes in blood pressure such as, for example, those referenced by illustrative points 512, 514, and 516. Time series 500 is observed to increase from point 512 to point 514 over a first time interval, and then decrease from point 514 to point 516 over a second time interval. The blood pressure value at point 516 may, for example, substantially correspond to the blood pressure value at point 512. In some embodiments, a new calibration at the time associated with point 514 may be desired as a result of the blood pressure change from point 512 to point 514. In some embodiments, a new calibration at the time associated with point 516 may be desired as a result of the blood pressure change from point 512 to point 514, and then to point 516. The blood pressure values included in time series 500 may be computed based at least in part on a DPTT measurement, which may be based at least in part on the signals of two PPG sensors placed at suitable locations on a patient.

Shown in illustrative FIGS. 5(b), 5(c), and 5(d) are illustrative graphs showing time series 520, 540, and 560, respectively. Time series 520, 540, and 560 may represent portions of one of the particular PPG signals used by the patient monitor to compute DPTT values and the blood pressure values of points 512, 514, and 516 of FIG. 5(a), respectively. Time series 520, 540, and 560, may each represent physiological pulses which may have occurred substantially at the times associated with points 512, 514 and 516, respectively. The ordinate of the illustrative graphs shown in FIGS. 5(b), 5(c), and 5(d) may be scaled in arbitrary units, while the abscissa of each of the graphs may be a normalized time variable. For example, an abscissa value of zero represents the onset of a particular pulse, and an abscissa value of one represents the end of a particular pulse, with reference to FIGS. 5(b), 5(c), and 5(d).

Figure 6:
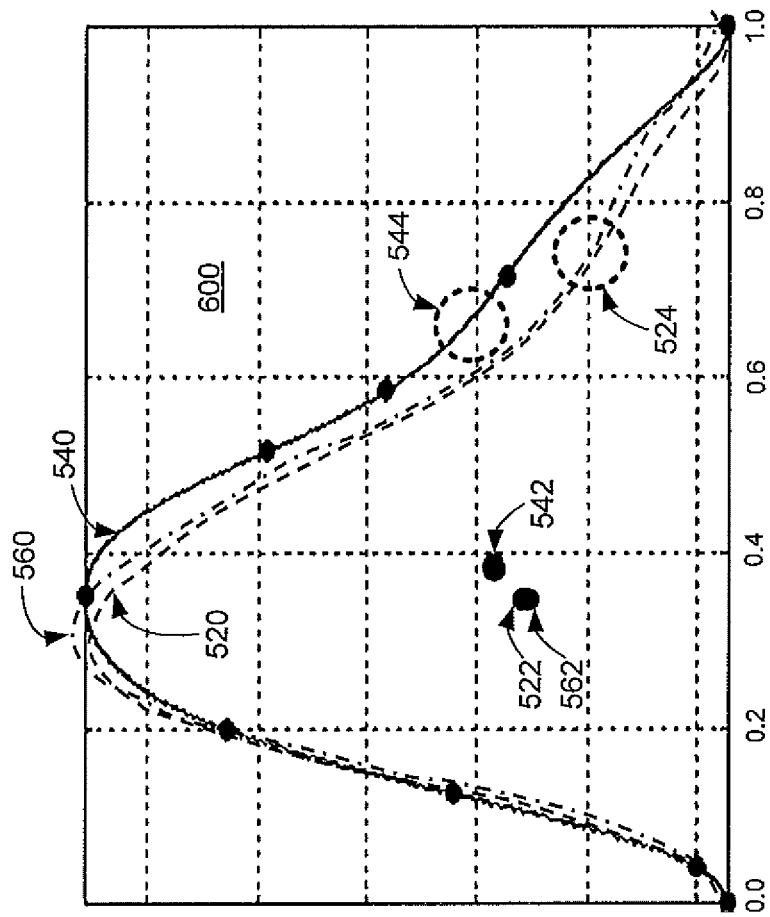
FIG. 6 shows a superposition of illustrative PPG signals of FIGS. 5(b)-5(d) in accordance with an embodiment.

Time series 520, 540, 560 may each have different morphologies due to, for example, physiological changes. In some embodiments, time series 520 and 560 may have substantially similar morphologies as each other, while time series 540 may have a relatively different morphology from both time series 520 and 560. Shown in FIG. 6 is superposition 600 of time series 520, 540, and 560 of FIGS. 5(b), 5(c), and 5(d), respectively. It can be seen in FIG. 6, that time series 520 and 560 have substantially similar morphologies to each other. It can also be seen in FIG. 6, that time series 540 has a substantially different morphology from both time series 520 and 560. For example, centroids 522 and 562 derived from time series 520 and 560, respectively, are substantially coincident with each other, and are both substantially different from centroid 542 derived from time series 540. In a further example, the dichrotic notches of time series 520 and 560 both lie substantially in notch region 524. The dichrotic notch of time series 540 lies substantially in notch region 544, located substantially apart from notch region 524.

Differences in metrics of one or more physiological signals such as, for example, centroids (e.g., centroids 522, 542, and 562) or dichrotic notch positions (e.g., within notch regions 524 or 544) of pulse waves of a PPG signal, may be monitored to determine when recalibration may be desirous. For example, a patient monitoring system may have particular calibration parameters at a time corresponding to point 512 of FIG. 5(a). Changes in arterial compliance, for example, may cause a change in blood pressure represented by the transition from point 512 to point 514 in FIG. 5(a). The transition from point 514 to point 516 may, in some embodiments, represent a return by the patient to a similar physiological state as that of point 512, indicated by the similar blood pressure values displayed at points 512 and 516.

The patient monitoring system may determine that the physiological state of the patient at point 516 is substantially similar to the physiological state of the patient at point 512. This determination may be based at least in part on the difference between the blood pressure values of points 512 and 516. For example, the patient monitoring system may compare the difference between the blood pressure values of points 512 and 516 to a threshold. If the difference is less than the threshold, the patient monitoring system may determine that the values correspond. The patient monitoring system may determine that the physiological states correspond based at least in part on the determination that the values correspond. The patient monitoring system may determine that the physiological states of the patient at points 512 and 516 correspond, and the patient monitoring system may not perform a calibration (e.g., a cuff inflation) at a time corresponding to point 516. Any suitable metrics, or combinations thereof, may be used to determine whether physiological states of a patient correspond.

In some embodiments, metrics associated with the blood pressure pattern from point 512 to point 514 to point 516 may be stored for later reference. For example, administration of a particular drug to a patient may cause the blood pressure change from point 512 to point 514, and then to point 516. Metrics associated with this blood pressure change such as, for example, the time interval between points 512 and 516, peak to peak difference, slope of the time series 500 computed at suitable points, any other suitable metrics, or any suitable combinations thereof, may be stored for future reference. For example, if the same drug is administered at a new time, a new calibration may not be required because stored calibration parameters corresponding to a previous calibration, performed during a previous drug administration, may be recalled. Because the previous calibration may have been performed during a similar physiological state (e.g., for a similar drug administration), the physiological signals may exhibit similar values of suitable metrics. In some embodiments, storing metrics associated with a physiological signal may reduce the desired number of calibrations of the patient monitoring system.

In reference to FIG. 6, a patient monitoring system may store one or more metrics associated with time trace 520 such as, for example, the position (abscissa and ordinate values) of centroid 522. The patient monitoring system may monitor a metric associated with a PPG signal such as, for example, the position of the centroid of a pulse wave. The relative centroid position may change from centroid 522 to centroid 542 then to centroid 562, as shown in FIG. 6. The position of centroid 562 may be determined by the patient monitoring system to correspond to the position of centroid 522. The determination may be based at least in part on, for example, differences between the abscissa and ordinate values of centroids 522 and 562. For example, the patient monitoring system may determine that the difference between both the abscissa and ordinate values of centroids 522 and 562 are both within a threshold (e.g., five percent), and accordingly that centroids 522 and 562 correspond to each other.

Figure 7:
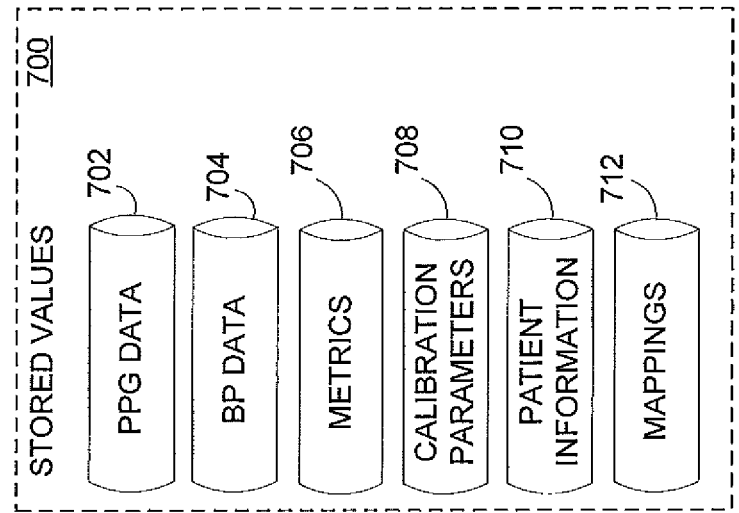
FIG. 7 is a block diagram of an illustrative database in accordance with an embodiment.

Shown in FIG. 7 is a block diagram of an illustrative database of stored values 700 in accordance with some embodiments. Stored values 700 may include PPG data 702, blood pressure data 704, metrics 706 derived from one or more PPG signals, patient monitoring system calibration parameters 708, patient information 710 (e.g., physiological information, patient history, multi-patient sample statistics), mappings 712, any other suitable data which may be stored in any suitable arrangement, or any suitable combinations thereof.

For example, PPG data 702 may include one or more data points sampled from a PPG signal, and stored in any suitable data format. PPG data 702 may include data sampled at any suitable sampling frequency, data sampled at irregular intervals, or both. In some embodiments, PPG data 702 may undergo mathematical manipulation such as, for example, smoothing, averaging (e.g., computing a moving average), re-sampling (e.g., sampling a subset of all data points), converting (e.g., non-dimensionalizing, normalized, offset shifted), any other suitable data processing technique, or any suitable combination thereof, prior to storage.

Blood pressure data 704 may include blood pressure measurements (e.g., a time series) computed from one or more received signals (e.g., invasive arterial sensors, PPG sensors, inflatable cuff sensors). Blood pressure data 704 may include, for example, systolic blood pressure, diastolic blood pressure, or both, or any suitable manipulation of any suitable blood pressure value. In some embodiments, blood pressure data 704 may be smoothed, averaged, re-sampled, converted, mathematically manipulated by any other suitable data processing technique or any combinations thereof.

Metrics 706 may include any suitable value which may be derived from any suitable signal (e.g., a PPG signal). For example, metrics 706 may include derivatives of any suitable order, integrals, statistics (e.g., mean, standard deviation, skew, kurtosis), regressions of any form and order, ordinate values, abscissa values, any other suitable metrics, evaluated at any suitable point or combination of points, which may be computed from a suitable signal, or any suitable combinations thereof. For example, in some embodiments, metrics 706 may include pulse rate, pulse wave area, dichrotic notch position, skew of a portion of a PPG signal, skew of the derivative of a portion of a PPG signal, upstroke length of a pulse wave, pulse wave height, pulse wave full width at half maximum (FWHM), any other suitable metric, or any suitable combinations thereof.

In some embodiments, PPG signals, data derived from any suitable signal, or combinations thereof, may be approximated by any suitable continuous or non-continuous function, basis set (e.g., orthogonal functions), expression, or suitable combination thereof in any suitable variable space. In some embodiments, for example, metrics 706 may include values, parameters, coefficients, boundary conditions, or other descriptors associated with a Fourier series, Fourier integral, Bessel function, Legendre polynomial, Chebyshev polynomial, Laguerre polynomial, discrete or continuous transform (e.g., Laplace, Fourier, wavelet), any other suitable basis set, expression, transform, or function, or any suitable combinations thereof. For example, the output of a fast Fourier transform (FFT) of portions of a sampled (e.g., discreet) PPG signal may be stored in accordance with metrics 706. In some embodiments, metrics 706 may include the coefficients $A_i$ (e.g., weighting functions, constants) of any suitable superposition (e.g., linear combination over index i) of expressions $f(x_j)$ depending on any suitable number of variables $x_j$, which may be used to approximate one or more values M of a metric, as illustratively shown by $$M \approx \sum_{i=1}^{N} A_i f_i(x_j). \tag{19}$$

A summation, such as that given by Eq. 19, may be used to approximate a portion of a signal (e.g., a signal feature corresponding to a physiological pulse), a metric time series, any other suitable values, or any combination thereof. It will be understood that the approximation sign in Eq. 19 may be replaced with an equal sign in suitable circumstances. In some embodiments, with reference to Eq. 19, more than one summation may be performed over any suitable number of indices.

Stored values 700 may include calibration parameters 708, which may be used to calibrate any suitable device (e.g., a sensor), system (e.g., a patient monitoring system), process, any other suitable hardware or software which may be used to perform a measurement, or any suitable combinations thereof. For example, in some embodiments, calibration parameters 708 may include a, b, and $c_i$ of Eqs. 14-18. Calibration parameters 708 may, for example, be stored and indexed with metrics computed substantially at a time when the calibration was performed.

Stored values 700 may include patient information 710, which may include inter-patient information, intra-patient information, patient histories, statistical information, any other information associated with one or more patients, or any combination of information thereof. For example, in some embodiments, patient information 710 may include patient medical histories, medication information, patient allergies, patient monitoring histories (e.g., previous physiological state information), patient identification information, any other suitable information, or any combination thereof.

Stored values 700 may include mappings 712, which may include any suitable type of distribution functions, functions with any suitable number of variables, expressions with any suitable number of variables, any other suitable correlations, or any suitable combinations thereof. In some embodiments, mappings 712 may include a probability distribution function (PDF), cumulative distribution function (CDF), conditional PDF, conditional CDF, multivariable function, differential equation, cross correlation, interpolation, any other suitable mathematical or computational tool for relating sets or variables, or any combinations thereof. For example, in some embodiments, mappings 712 may include a function such as that given by $$M \approx f(x_1, x_2, \ldots, x_N), \quad (20)$$

wherein $x_i$ may be suitable parameters, metrics, or other values, and M may be any suitable metric value. In a further example, only discreet values of values $x_i$ may be defined (e.g., only integers, evenly spaced discreet values), and a suitable interpolation may be used to determine M values based on $x_i$ values intermediate to the discreet $x_i$ values. It will be understood that the approximation sign in Eq. 20 may be replaced with an equal sign in suitable circumstances.

Stored values 700 may be stored in any suitable memory device or combination of memory devices. Stored values 700 may be stored remotely (e.g., in remote memory 90 of FIG. 1), locally (e.g., in ROM 52 of FIG. 1), or any suitable combination thereof. For example, in some embodiments, a database of stored values 700 may be catalogued and indexed as a lookup table, in which stored values 700 may be stored in one or more memory devices. Any suitable data structure may be used to index stored values 700, including, for example, tree structures, array structures (e.g., vectors, images), mappings, any other suitable data structure, or any suitable combinations thereof. Any of stored values 700 may be associated, indexed, catalogued, or otherwise related to any other of stored values 700. For example, a particular value of metric 706 may be associated with a particular set of calibration parameters 708. The particular set calibration parameters 708 may be recalled by the patient monitoring system if a monitored metric is determined to substantially correspond to the particular value of metric 706.

In some embodiments, a patient monitoring system may decide not to perform a calibration if it determines that a monitored metric corresponds to a particular value of a stored metric 706. In some embodiments, a patient monitoring system may determine that the current calibration parameters are appropriate based at least in part on values of one or more monitored metrics. For example, a patient monitoring system may determine that a patient's current physiological state corresponds to a previous physiological state of the patient. If, for example, the current calibration parameters were taken during the previous physiological state, and are still appropriate, the patient monitoring system may determine that a recalibration is not desired.

Figure 8:
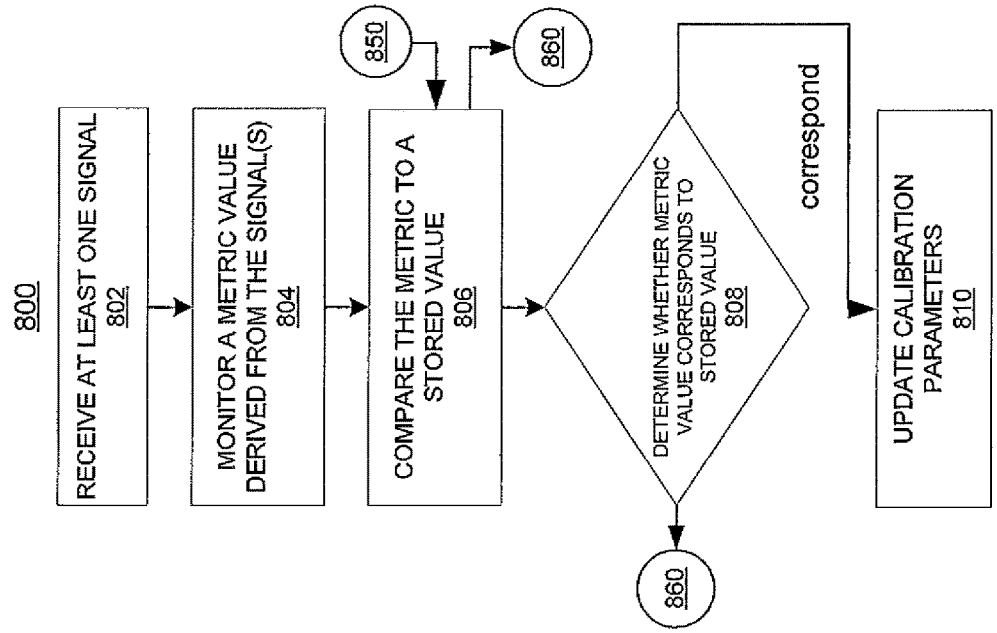
FIG. 8 is a flow diagram of illustrative steps for updating monitoring system calibration parameters in accordance with an embodiment.

Shown in FIG. 8 is flow diagram 800 of an illustrative process for updating monitoring system calibration parameters in accordance with an embodiment. Illustrative step 802 may include receiving at least one signal to the signal input of a patient monitoring system (e.g., patient monitoring system 10 of FIG. 1). Illustrative step 804 may include monitoring the value of at least one metric derived from the received signal (e.g., a PPG signal). Illustrative step 806 may include comparing the monitored metric value to a stored value (e.g., any of stored values 700 of FIG. 7). Illustrative determination step 808 may include determining whether the monitored metric value corresponds to the stored value. Illustrative step 810 may include updating calibration parameters of a patient monitoring system (e.g., patient monitoring system 10 of FIG. 1).

Step 802 of FIG. 8 may include receiving any suitable physiological signal such as, for example, a PPG signal. In some embodiments, the signal may be sampled at any suitable sampling frequency by a patient monitoring system. In some embodiments, more than one signal may be received in accordance with step 802. For example, in some embodiments, two PPG signals may be received by a patient monitoring system (e.g., to calculate a DPTT value).

Step 804 of FIG. 8 may include monitoring any suitable metric value which may be derived from a received signal (e.g., the signal of step 802). For example, the value of metrics such as blood pressure, heart rate, DPTT, signal morphology (e.g., pulse wave area, pulse wave moment, relative fiducial point position), any other suitable metrics, or any suitable combinations thereof, may be monitored by a patient monitoring system at step 804. In some embodiments, step 804 may include a patient monitoring system storing, recalling, deleting, displaying or otherwise managing metric values derived from any suitable received signal. For example, in some embodiments, a patient monitoring system may store a metric value in queue (e.g., in a suitable memory device), and replace the value with a new value at a later time.

Step 806 of FIG. 8 may include comparing a monitored metric value (e.g., metric value of step 804) to a stored value (e.g., any of stored values 700 of FIG. 7). In some embodiments, step 806 may include determining a difference between a monitored metric value and a stored value. The difference may include computations such as subtraction, normalization, division, any other suitable operation, or any suitable combination thereof, of the monitored metric value and the stored value. In some embodiments, a difference may be compared to a threshold value. The threshold value may, for example, be a stored value, a user defined value, a substantially real-time value computed based at least in part on a received signal, a monitored metric, a value derived from any other formulation, or any suitable combination thereof. In some embodiments, the stored value may be recalled from any suitable database(s) stored in suitable memory device(s), as shown illustratively by step 850. Step 850 may include parsing data, interpolating data, requesting values, searching data structures, traversing data structures (e.g., arrays, trees, multimaps), any other suitable technique for accessing a stored value, or any suitable combination thereof.

In some embodiments, any suitable pattern matching technique, pattern recognition technique, or other classification technique, or combination of techniques, may be used to compare metricsat step 806 of FIG. 8. For example, templates, classifications (e.g., k-nearest neighbor algorithms, decision trees), regressions (e.g., neural networks), any other pattern recognition techniques, or any suitable combination thereof may be used to compare or match the value of a monitored metric to a stored value.

Figure 10:
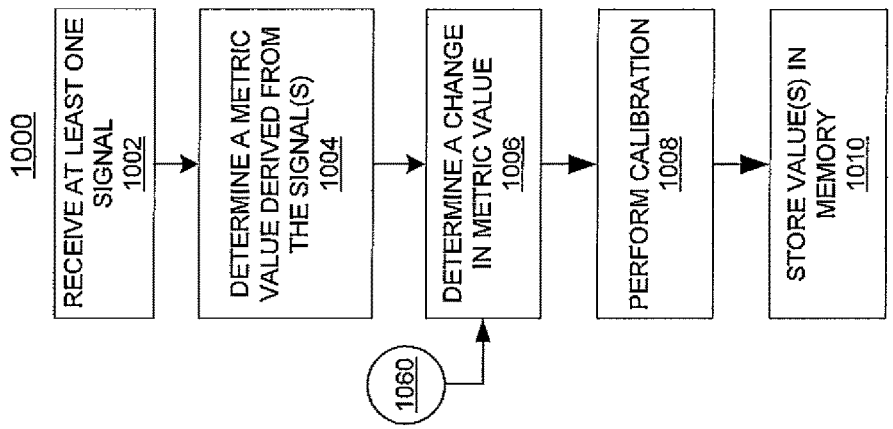
FIG. 10 is a flow diagram of illustrative steps for storing physiological signals and metrics associated with a calibration in accordance with an embodiment.

If the patient monitoring system does not locate a suitable stored value, step 860 may be performed (see step 1060 of flow diagram 1000 of FIG. 10). Step 860 may include determining a morphology change, performing a calibration, storing values in memory, any other suitable actions, or any combination thereof. For example, if the patient monitoring system cannot locate a suitable stored value for comparison, the patient monitoring system may store one or more current metric values so that stored metric values may be available in the future.

Determination step 808 of FIG. 8 may include, for example, determining whether a monitored metric value corresponds to a stored metric value. In some embodiments, a comparison of the monitored metric value and the stored value may be used at determination step 808. For example, in some embodiments, a monitored metric value may be determined to correspond to a stored value if a computed difference between the two values is less than a particular threshold value.

It may be determined, for example, at determination step 808 that a monitored metric does not correspond to a stored value. In response to such a determination, the patient monitoring system may, in some embodiments, initiate step 802, 804, or 806. In some embodiments, the monitored metric value may be compared to further stored values at step 808. In some embodiments, the patient monitoring system may compute a new value for the monitored metric and compare the new value to a stored value at determination step 808.

In some embodiments, the patient monitoring system may determine that a monitored metric does not correspond to a stored value. In response to such a determination, the patient monitoring system may, in some embodiments, perform step 860 (see step 1060 of flow diagram 1000 of FIG. 10). For example, the patient monitoring system may determine that the monitored metric does not correspond to a stored value, and that a calibration is desired. One or more metric values corresponding to the calibration may be stored for future reference as stored values.

If the value of a monitored metric is determined to correspond to a stored value, calibration parameters may be updated in accordance with step 810 of FIG. 8. Step 810 may include, for example, recalling calibration parameters (e.g., a, b and/or $c_i$ of Eqs. 14-18) from a memory device, replacing calibration parameters with stored calibration parameters, determining a blood pressure measurement based on stored calibration parameters, any other suitable process, or any suitable combination thereof. In some embodiments, calibration parameters associated with the stored value may be recalled and used in the current calibration.

In an illustrative example, two PPG signals may be received by a patient monitoring system (e.g., patient monitoring system 10 of FIG. 1) at step 802 of FIG. 8. A metric such as, for example, the DPTT derived from the received signals may be computed as a time series by the patient monitoring system at step 804 of FIG. 8. The patient monitoring system may compare one or more DPTT values to a suitable stored DPTT value in a suitable memory device (e.g., ROM 52, remote memory 90, or both, of FIG. 1). The stored DPTT value may be recalled by the patient monitoring system by suitable searching of a catalogue of stored metric values stored in a suitable database. If the patient monitoring system determines that the monitored DPTT value corresponds substantially to a stored DPTT value, the patient monitoring system may recall calibration parameters associated with the stored DPTT value. The patient monitoring system may update the current blood pressure calibration values (e.g., a, b and/or $c_i$ of Eqs. 14-18) with the blood pressure calibration values associated with the stored DPTT value. Although the previous example discloses monitoring a DPTT value and updating blood pressure calibration parameters, the value of any suitable metric may be monitored, and any suitable calibration parameters may be updated.

Figure 9:
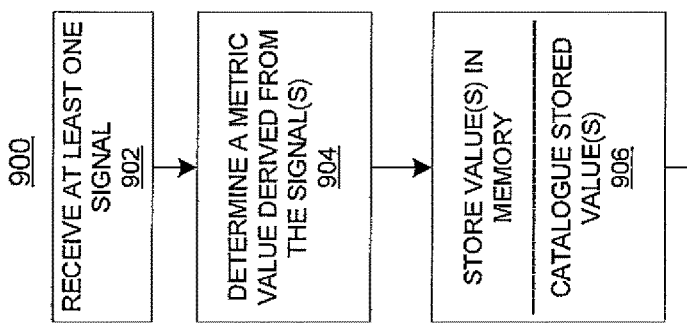
FIG. 9 is a flow diagram of illustrative steps for storing physiological signals and metrics in accordance with an embodiment.

Shown in FIG. 9 is flow diagram 900 of an illustrative process for storing physiological signals, metrics, or both, in accordance with an embodiment. Illustrative step 902 may include a patient monitoring system (e.g., patient monitoring system 10 of FIG. 1) receiving at least one signal. Illustrative step 904 may include computing the value of at least one metric based at least in part on the received signal (e.g., a PPG signal). Illustrative step 906 may include storing the monitored metric value in any suitable memory device (e.g., ROM 52, remote memory 90, or both, of FIG. 1). Illustrative determination step 908 may include cataloguing the stored metric value in a suitable database.

Step 902 of FIG. 9 may include receiving any suitable physiological signal such as, for example, a PPG signal. In some embodiments, the signal may be sampled at any suitable sampling frequency allowing the signal to be monitored by a patient monitoring system. In some embodiments, more than one signal may be received at step 902. For example, in some embodiments, two PPG signals may be received by a patient monitoring system.

Step 904 of FIG. 9 may include determining (e.g., computing) any suitable metric value that may be derived from a received signal of step 902. For example, the value of metrics such as blood pressure, pulse rate, DPTT, signal morphologies (e.g., pulse wave area, pulse wave moment, relative fiducial point position, skewness, kurtosis), any other suitable metrics, or any combinations thereof, may be monitored by a suitable patient monitoring system at step 904. In some embodiments, a patient monitoring system may store (e.g., to a queue), recall (e.g., from a queue), delete, display or otherwise manage one or more metric values derived at least in part from any suitable received signal at step 904.

Step 906 of FIG. 9 may include storing, cataloguing, or both, any suitable metric value in any suitable memory storage device. For example, in some embodiments, a patient monitoring system may create or addend a database any of stored values 700 of FIG. 7. For example, in some embodiments, patient information 710 may be appended with information regarding a new patient. In a further example, multiple values of a particular metric may be stored and used as a training set on which a correlation or PDF may be based.

In some embodiments, metric values may be stored and then catalogued (e.g., indexed by value and storage location). In some embodiments, metric values may be catalogued and then stored (e.g., stored in particular locations based at least in part on metric value). Metric values may be associated with any of stored values 700 during cataloguing, in some embodiments.

In some embodiments, step 950 of FIG. 9 may correspond substantially to step 850 of FIG. 8. For example, values catalogued, stored, or both, at step 906 of FIG. 9 may be recalled or otherwise identified at step 806 of FIG. 8. In some embodiments, a suitable combination of steps 850 and 950 may allow a suitable database to be created, appended, or otherwise maintained, and any data stored within to be recalled at a suitable time (e.g., in response to a request).

Shown in FIG. 10 is flow diagram 1000 of an illustrative process for storing physiological signals, metrics, or both, corresponding to a calibration in accordance with an embodiment. Illustrative step 1002 may include a patient monitoring system (e.g., patient monitoring system 10 of FIG. 1) receiving at least one signal. Illustrative step 1004 may include computing the value of at least one metric based at least in part on the at least one received signal (e.g., a PPG signal). Illustrative determination step 1006 may include determining a change in one or more metric values. Illustrative determination step 1008 may include calibrating one or more sensors of a patient monitoring system. Illustrative step 1010 may include storing one or more metric value in any suitable memory device (e.g., ROM 52, remote memory 90, or both, of FIG. 1).

Step 1002 of FIG. 10 may include receiving any suitable physiological signal such as, for example, a PPG signal. In some embodiments, the signal may be sampled at any suitable sampling frequency allowing the signal to be monitored by a patient monitoring system. In some embodiments, more than one signal may be received at step 1002. For example, in some embodiments, two PPG signals may be received by a patient monitoring system.

Step 1004 of FIG. 10 may include determining (e.g., computing) any suitable metric value that may be derived from a received signal of step 1002. For example, the value of metrics such as blood pressure, pulse rate, DPTT, signal morphologies (e.g., pulse wave area, pulse wave moment, relative fiducial point position, skewness, kurtosis), any other suitable metrics, or any combinations thereof, may be monitored by a suitable patient monitoring system at step 1004. In some embodiments, a patient monitoring system may store (e.g., to a queue), recall (e.g., from a queue), delete, display or otherwise manage one or more metric values derived at least in part from any suitable received signal at step 1004.

Step 1006 may include determining a change in one or more metric values. In some embodiments, a change in one or metric values may be a change from a constant or historical metric values. In some embodiments, a change in metric value may be a change in a derivative of one or more metrics. The value of one or more metrics may be compared to a threshold to aid in determining whether the metric value has changed. For example, if the difference between a monitored metric value and threshold value is computed to be greater than ten percent of the monitored metric value, the patient monitoring system may determine that the monitored metric has changed. In some embodiments, a user (e.g., a clinician) may determine that a metric value has changed and the patient monitoring system may receive user input indicating the change.

In some embodiments, a stored value may not be available at step 1006 to aid in determining whether a metric has changed. For example, the patient monitoring system may determine that one or more particular metric values do not correspond to any available stored values. For example, the patient monitoring system may determine that the blood pressure has changed if the blood pressure measurement changes by more than one standard deviation from a historical measurement (e.g., a time series of blood pressure measurements). In some embodiments, step 860 of FIG. 8 may correspond to step 1060 of FIG. 10.

Step 1008 of FIG. 10 may include performing a calibration measurement if one or more metric values are determined to have changed. The calibration may include performing a NIBP measurement, updating a measurement (e.g., a displayed blood pressure measurement), calibrating one or more devices (e.g., two PPG sensors), any other suitable action, or any combination thereof.

In some embodiments, step 1008 may be performed in response to a lack of stored values being available. For example, if a particular metric is determined to have changed, but no stored values are available which correspond to the metric value, the patient monitoring system may perform a calibration (e.g., perform a cuff inflation).

Step 1010 of FIG. 10 may include storing metric values, calibration parameters, or both, in any suitable memory storage device. In some embodiments, step 1010 may append a database such as a look-up table with one or more metric values, calibration parameters, signal values, any other suitable values associated with the calibration of step 1008, or any combination thereof. In some embodiments, step 1010 may allow one or more current metrics to be stored for future reference. For example, in some embodiments, a patient monitoring system may create or addend a database any of stored values 700 of FIG. 7. For example, in some embodiments, patient information 710 may be appended with information regarding a new patient. In a further example, multiple values of a particular metric may be stored and used as a training set on which a correlation or PDF may be based.

In some embodiments, metric values may be stored and then catalogued (e.g., indexed by value and storage location). In some embodiments, metric values may be catalogued and then stored (e.g., stored in particular locations based at least in part on metric value). Metric values may be associated with any of stored values 700 during cataloguing, in some embodiments.

It will be understood that the steps of flow diagrams 800, 900, and 1000 of FIGS. 8-10, respectively, are illustrative. Any of the steps of flow diagrams 800, 900, and 1000 may be modified, omitted, rearranged, combined with other steps of flow diagrams 800, 900, and 1000, or supplemented with additional steps, without departing from the scope of the present disclosure.

What is claimed is:

1. A method for triggering a cuff-based blood pressure measurement of a subject, the method comprising:
   receiving a photoplethysmograph (PPG) signal from a sensor;
   monitoring, using a processor, a first value of a metric derived at least in part from the PPG signal;
   comparing, using the processor, the first value of the metric to each stored value of a plurality of stored values, wherein each stored value of the plurality of stored values is associated with a respective calibration parameter;
   determining, using the processor, that the first value of the metric does not correspond to any stored value of the plurality of stored values based at least in part on the comparison;
   triggering, using the processor, the cuff-based blood pressure measurement in response to determining that the first value of the metric does not correspond to any stored value of the plurality of stored values;
   executing, using an inflatable cuff, the cuff-based blood pressure measurement of the subject in response to the trigger;
   determining, using the processor, a second value of the metric;
   comparing, using the processor, the second value of the metric to stored values of the plurality of stored values;

determining, using the processor, that the second value of the metric corresponds to a stored value of the plurality of stored values based at least in part on the comparison; and recalling, from at least one memory device, a set of blood pressure calibration parameters associated with the stored value of the plurality of stored values based on determining that the second value of the metric corresponds to the stored value.

2. The method of claim 1, further comprising updating, using the processor, the plurality of stored values to include the first value of the metric in response to the trigger.

3. The method of claim 2, further comprising updating, using the processor, a stored set of blood pressure calibration parameters comprising the calibration parameters associated with the plurality of stored values, based at least in part on the cuff-based blood pressure measurement of the subject, to generate an updated stored set of blood pressure calibration parameters, wherein the stored set of blood pressure calibration parameters comprises the set of blood pressure calibration parameters associated with the stored value.

4. The method of claim 3, further comprising determining, using the processor, a blood pressure value of the subject based on the updated stored set of blood pressure calibration parameters and the PPG signal.

5. The method of claim 4, wherein the cuff-based blood pressure measurement comprises a cuff-based blood pressure measurement, the method further comprising:
comparing the blood pressure value of the subject to a stored blood pressure value of the subject;
determining, using the processor, that a difference between the blood pressure value and the stored blood pressure value satisfies a threshold difference value; and
triggering, using the processor, a second cuff-based blood pressure measurement based at least in part on the determination.

6. The method of claim 3, further comprising storing, using the at least one memory device, the updated set of stored blood pressure calibration parameters and the first value of the metric.

7. The method of claim 1, wherein the first value of the metric corresponds to pulse wave area, pulse wave moment, relative fiducial point position, kurtosis, dicrotic notch position, pulse wave skew, skew of the derivative of a portion of the PPG signal, pulse wave height, pulse wave full width at half maximum, length of a pulse upstroke, the position of a centroid of a pulse wave, or any combination thereof.

8. The method of claim 1, wherein the first value of the metric corresponds to blood pressure, heart rate, differential pulse transit time, or any combination thereof.

9. The method of claim 1, wherein comparing the first value of the metric to each stored value of the plurality of stored values comprises using a pattern matching technique.

10. The method of claim 1, further comprising receiving an auxiliary PPG signal from a sensor, wherein the metric corresponds to a time difference between at least one portion of the PPG signal and at least one portion of the auxiliary PPG signal.

11. The method of claim 1, further comprising calibrating a system comprising the sensor using the cuff-based blood pressure measurement of the subject.

12. A system for triggering a cuff-based blood pressure measurement of a subject, the system comprising:
a signal input configured to receive a PPG signal of a subject from a sensor;
a processor coupled to the signal input, wherein the processor is configured to:
monitor a first value of a metric derived at least in part from the PPG signal;
compare the first value of the metric to each stored value of a plurality of stored values, wherein each stored value of the plurality of stored values is associated with a respective calibration parameter;
determine that the first value of the metric does not correspond to any stored value of the plurality of stored values based at least in part on the comparison;
trigger the cuff-based blood pressure measurement in response to determining that the first value of the metric does not correspond to any stored value of the plurality of stored values;
determine a second value of the metric;
compare the second value of the metric to stored values of the plurality of stored values;
determine that the second value of the metric corresponds to a stored value of the plurality of stored values based at least in part on the comparison; and
recall, from at least one memory device, a set of blood pressure calibration parameters associated with the stored value of the plurality of stored values based on determining that the second value of the metric corresponds to the stored value; and
an inflatable cuff coupled to the processor, wherein the inflatable cuff is configured to execute the cuff-based blood pressure measurement of the subject in response to the trigger.

13. The system of claim 12, wherein the processor is further configured to update the plurality of stored values to include the first value of the metric in response to the trigger.

14. The system of claim 13, wherein the processor is further configured to update a stored set of blood pressure calibration parameters comprising the calibration parameters associated with the plurality of stored values, based at least in part on the cuff-based blood pressure measurement of the subject, to generate an updated stored set of blood pressure calibration parameters, wherein the stored set of blood pressure calibration parameters comprises the set of blood pressure calibration parameters associated with the stored value.

15. The system of claim 14, wherein the processor is further configured to determine a pressure value of the subject based on the updated stored set of blood pressure calibration parameters and the PPG signal.

16. The system of claim 15, wherein the processor is further configured to:
compare the blood pressure value of the subject to a stored blood pressure value of the subject;
determine that a difference between the blood pressure value of the subject and the stored blood pressure value of the subject satisfies a threshold difference value; and
trigger a cuff-based blood pressure measurement based at least in part on the determination.

17. The system of claim 12, wherein the sensor comprises a first sensor, and wherein the signal input is further configured to receive a PPG signal of a subject from a second sensor.

18. The system of claim 12, wherein the metric comprises at least one of a differential pulse transit time, blood pressure, heart rate, PPG signal morphology metric, PPG signal integral, PPG signal moment, PPG signal peak value, coefficient of a PPG signal transform, or a combination thereof.

19. The system of claim 12, wherein the processor is configured to compare the value of the metric to each stored value of the plurality of stored values by at least using a pattern matching technique.

20. The system of claim 12, wherein the processor is further configured to calibrate a system comprising the sensor using the cuff-based blood pressure measurement of the subject.

* * * * *